United States Patent
Vachon et al.

(10) Patent No.: US 6,405,091 B1
(45) Date of Patent: Jun. 11, 2002

(54) LEAD ASSEMBLY WITH MASKED MICRODISK TIP ELECTRODE AND MONOLITHIC CONTROLLED RELEASE DEVICE

(75) Inventors: David J. Vachon, Granada Hills; Shahram Moaddeb, Woodland Hills; Gene A. Bornzin; Kevin L. Morgan, both of Simi Valley, all of CA (US)

(73) Assignee: Pacesetter, Inc., Sylmar, CA (US)

(*) Notice: Subject to any disclaimer, the term of this patent is extended or adjusted under 35 U.S.C. 154(b) by 0 days.

(21) Appl. No.: 09/359,327

(22) Filed: Jul. 20, 1999

(51) Int. Cl.[7] .................................................. A61N 1/05
(52) U.S. Cl. ...................................... 607/120; 607/126
(58) Field of Search ................................. 607/120, 126, 607/128

(56) References Cited

U.S. PATENT DOCUMENTS

| | | | | |
|---|---|---|---|---|
| 3,835,864 A | * | 9/1974 | Rasor et al. ................ 128/419 |
| 3,902,501 A | | 9/1975 | Citron et al. ................ 128/418 |
| 3,939,843 A | | 2/1976 | Smyth ........................ 128/404 |
| 4,233,992 A | | 11/1980 | Bisping ....................... 128/785 |
| 4,301,815 A | | 11/1981 | Doring ........................ 128/785 |
| 4,360,031 A | * | 11/1982 | White ......................... 128/786 |
| 4,502,492 A | | 3/1985 | Bornzin ...................... 128/785 |
| 4,506,680 A | | 3/1985 | Stokes ........................ 128/786 |
| 4,519,404 A | | 5/1985 | Fleischhacker ............. 128/785 |
| 4,542,752 A | | 9/1985 | Dehaan et al. .............. 128/784 |
| 4,577,642 A | | 3/1986 | Stokes ........................ 128/784 |
| 4,722,353 A | * | 2/1988 | Sluetz ........................ 128/785 |
| 4,796,643 A | | 1/1989 | Nakazawa et al. .......... 128/785 |
| 4,844,099 A | | 7/1989 | Skalsky et al. ............. 128/785 |
| 4,945,922 A | | 8/1990 | van Krieken ............... 128/785 |
| 5,097,843 A | | 3/1992 | Soukup et al. .............. 128/794 |
| 5,238,007 A | | 8/1993 | Giele et al. ................. 607/126 |
| 5,282,844 A | | 2/1994 | Stokes ........................ 607/120 |
| 5,300,107 A | * | 4/1994 | Stokes et al. ............... 607/126 |
| 5,330,520 A | | 7/1994 | Maddison et al. .......... 607/122 |
| 5,408,744 A | | 4/1995 | Gates ........................... 29/875 |
| 5,447,529 A | | 9/1995 | Marchlinski et al. ........ 607/99 |
| 5,755,767 A | * | 5/1998 | Doan et al. ................. 607/126 |
| 5,871,529 A | | 2/1999 | Bartig et al. ............... 607/122 |
| 6,006,139 A | * | 12/1999 | Kruse et al. ................ 607/125 |

FOREIGN PATENT DOCUMENTS

| | | | |
|---|---|---|---|
| EP | 428812 | 5/1991 | ............. 607/122 |
| GB | 2065478 | 7/1981 | ............. 607/123 |
| JP | 6-47095 | 2/1994 | ............. 607/122 |
| NL | 7909050 | 6/1980 | ............. 607/126 |
| WO | WO93/00130 | 1/1993 | ............. 607/128 |

* cited by examiner

Primary Examiner—Carl Layno

(57) ABSTRACT

A passive fixation, body implantable lead assembly has a cylindrical tip electrode whose outer side surface is covered with a thin dielectric insulating layer so as to mask an active, disk-shaped electrode surface at the distal extremity of the tip electrode. The active electrode surface preferably has an area less than about 1 mm$^2$. An MCRD, in the form of a collar, may be carried by a proximal portion of the tip electrode. Supplementing a set of main tines projecting from the distal end portion of an insulating sheath housing the lead assembly is a set of nubby auxiliary tines extending from the sheath immediately adjacent the distal extremity thereof.

23 Claims, 3 Drawing Sheets

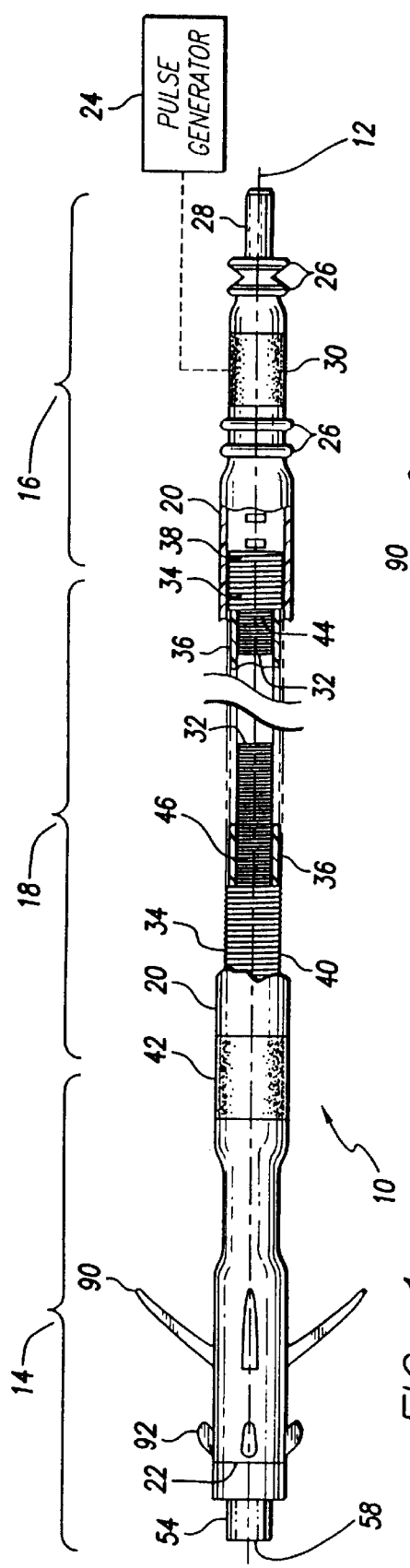
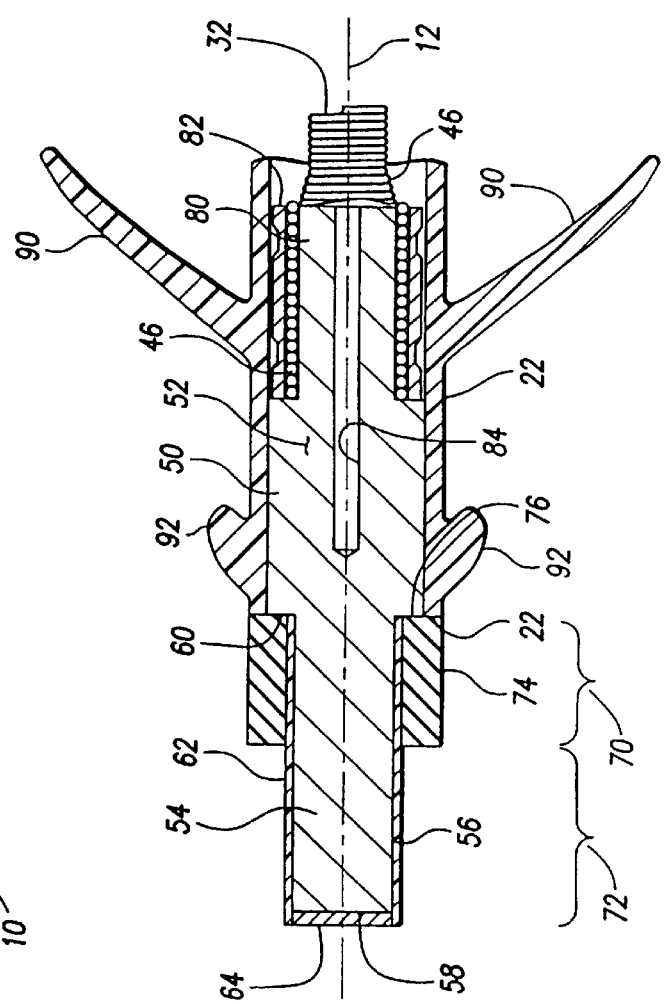
FIG. 1
FIG. 2

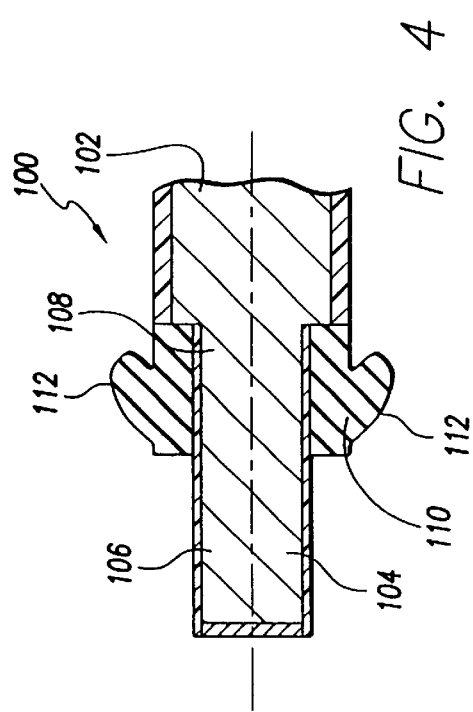
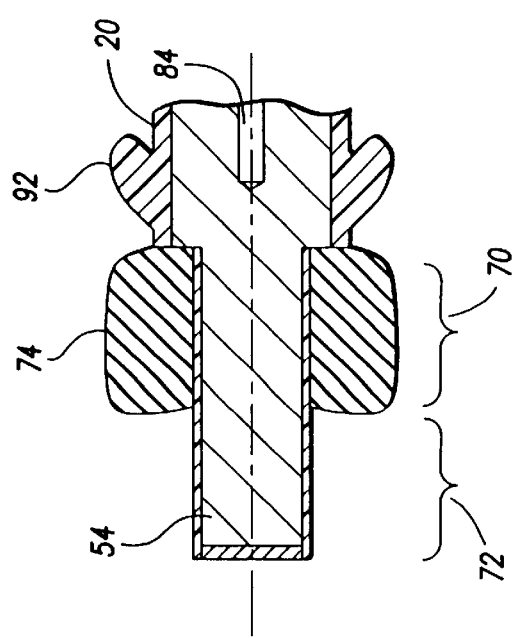
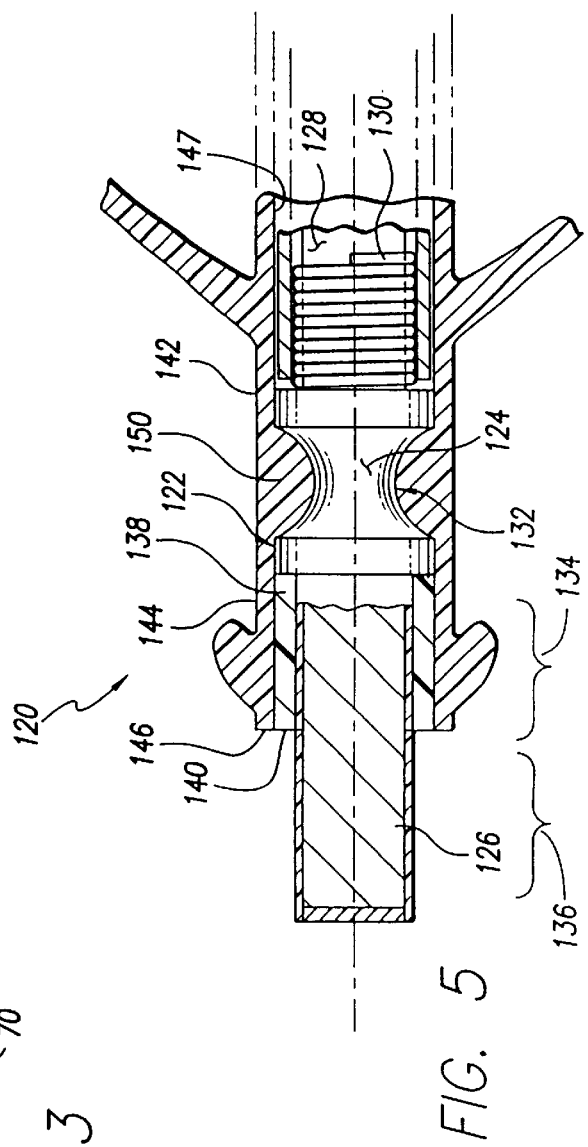

LEAD ASSEMBLY WITH MASKED MICRODISK TIP ELECTRODE AND MONOLITHIC CONTROLLED RELEASE DEVICE

FIELD OF THE INVENTION

The present invention relates generally to implantable medical devices for providing stimulating pulses to selected body tissue, and more particularly, to the lead assemblies connecting such devices with the tissue to be stimulated.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart and representing cardiac activity, or for both pacing and sensing in which case a single lead serves as a bidirectional pulse transmission link between the pacemaker and the heart. An endocardial type lead, that is, a lead which is inserted into a vein and guided therethrough into a cavity of the heart, includes at its distal end a tip electrode designed to intimately contact the endocardium, the tissue lining the inside of the heart. The lead further includes a proximal end having a connector pin adapted to be received by a mating socket in the pacemaker. A flexible, coiled conductor surrounded by an insulating tube or sheath couples the connector pin at the proximal end and the electrode at the distal end.

To prevent displacement or dislodgment of the tip electrode and to maintain the necessary stable electrical contact between the tip electrode and the endocardial tissue, the electrode must be firmly anchored relative to the tissue. A number of methods, both passive and active, have been devised for this purpose. In accordance with one known passive fixation technique, a plurality of flexible tines are molded integrally with the insulative sheath covering the coiled electrical conductors and extend rearwardly at an acute angle relative to the longitudinal axis of the lead. Following implantation of the lead, the tines become entangled in the trabecular network thereby securing the electrode position. Since the tines can flatten against the lead body and thus reduce its diameter, tined leads are often suitable for introduction through small blood veins. Other known passive fixation techniques include collar electrodes which have one or more conical projections of silicon rubber or other biocompatible flexible material behind the electrode tip. Like the tines, the cone becomes entangled in the trabecular network inside the heart, thereby anchoring the electrode tip. In yet another known approach which is advantageous if relocation of the electrode tip becomes necessary, projecting, flexible fins are used to provide stable anchoring. It is known, however, that even small displacements or "microdisiodgments" of the tip electrode can result in sporadic losses of reliable electrical contact between the tip electrode and the tissue engaged thereby resulting in increases in the stimulation voltage.

The optimization of the design of a passive fixation tip electrode depends on many factors. If the surface area of an electrode is too great too much current is drained from the battery due to low impedances. Alternatively, if the electrode area is not great enough excessive voltage is necessary in order to deliver the proper current flux density required for stimulation. An optimal electrode in terms of surface area minimizes both the voltage and current required for stimulation. Similarly, shape plays an important role in the determination of the effectiveness of the electrode. An optimized electrode shape, for a given electrode surface area, minimizes the current and voltage required for stimulation while providing the necessary current flux density for stimulation.

The presence of a steroidal anti-inflammatory, such as dexamethasone, is known to reduce the threshold for stimulation by minimizing fibrotic encapsulation or fibrosis which occurs toward the end of any normal healing response to the implant of an electrode. This minimization of fibrosis allows the electrode and excitable tissue to be in closer proximity, the result of this suppressed foreign body reaction being lower voltage and current requirements at threshold. Thus, steroid eluting tip electrodes can be made smaller than their nonsteroid counterparts and therefore will present higher pacing impedances and afford lower voltage thresholds, minimizing current drain and preserving battery life. Such electrode structures are disclosed, for example, in U.S. Pat. Nos. 5,282,844 and 5,408,744.

Despite the advances that have been made in this field, there remains a need for lead assemblies having tip electrode structures that minimize both the voltage and current required for stimulation so as to preserve battery life.

SUMMARY OF THE INVENTION

In accordance with one exemplary embodiment of the present invention, there is provided a passive fixation, body implantable lead assembly adapted to transmit electrical signals between a proximal end portion of the lead assembly and a distal end portion of the lead assembly and to thereby stimulate selected body tissue and/or sense electrical signals therefrom. The lead assembly has a longitudinal axis and comprises an electrical conductor extending between the proximal and distal end portions of the lead assembly for transmitting the electrical signals, a sheath of insulative, biocompatible, biostable material enclosing the electrical conductor, and a tip electrode electrically connected to the distal end of the electrical conductor. In accordance with a preferred form of the invention, the tip electrode is in the form of a cylinder disposed coaxially of the longitudinal axis of the lead assembly, and has a side surface and a distal extremity. The distal extremity of the tip electrode comprises a generally planar, disk shaped active electrode surface extending substantially perpendicular to the longitudinal axis of the assembly. Last, a thin dielectric insulating layer covers substantially the entire side surface of the tip electrode. By so masking the active electrode surface of the tip electrode with a dielectric insulator, the pacing impedance and current density of the electrode may be substantially increased. Further improvements in this connection may be achieved by reducing the active electrode surface area to less than about 1 $mm^2$.

In accordance with another aspect of the invention, the side surface of the tip electrode includes a distal portion and a proximal portion and a drug dispensing member is disposed around the proximal portion of the tip electrode for storing a drug to be dispensed to the body tissue. Such a drug dispensing member preferably takes the form of a collar adapted to be loaded with, for example, a steroidal anti-inflammatory such as dexamethasone which serves to reduce the stimulation threshold by minimizing fibrosis.

In accordance with yet another aspect of the present invention, the sheath may include a first set of anchoring tines extending outwardly from the sheath, the first set of tines being disposed adjacent the distal extremity of the sheath. A second set of anchoring tines extends outwardly from the sheath and away from the tip electrode to form an acute angle with the sheath material, the second set of tines being disposed proximally of the first set tines along the distal end portion of the lead assembly. The tines of the first set of tines have a length less than that of the second set of tines. By increasing the surface area of the distal portion of the lead assembly engaging the trabecular network inside the heart, the "nubby" first set of tines tends to increase the stability of lead fixation to avoid microdislodgments of the tip electrode which may cause sporadic increases in stimulation voltage.

BRIEF DESCRIPTION OF THE DRAWINGS

Further objects, features and advantages of the invention will become apparent from the Detailed Description of the Preferred Embodiments, below, when read in conjunction with the accompanying drawings, in which:

FIG. 1 is a side view, partly in cross section, of a bipolar pacing lead assembly in accordance with a first exemplary embodiment of the present invention;

FIG. 2 is a side view, partly in cross section, of the distal end portion of the lead assembly of FIG. 1 showing, among other features, a drug dispensing member or monolithic controlled release device (MCRD) carried by the tip electrode of the lead assembly;

FIG. 3 is a side view, in cross section, of a portion of the assembly of FIG. 2 showing the drug dispensing member in a swelled state;

FIG. 4 is a side view, in cross section, of the distal end portion of a lead assembly in accordance with a second embodiment of the invention;

FIG. 5 is a side view, in cross section, of the distal end portion of a lead assembly in accordance with a third embodiment of the invention;

DETAILED DESCRIPTION OF THE PREFERRED EMBODIMENTS

Figure 7:
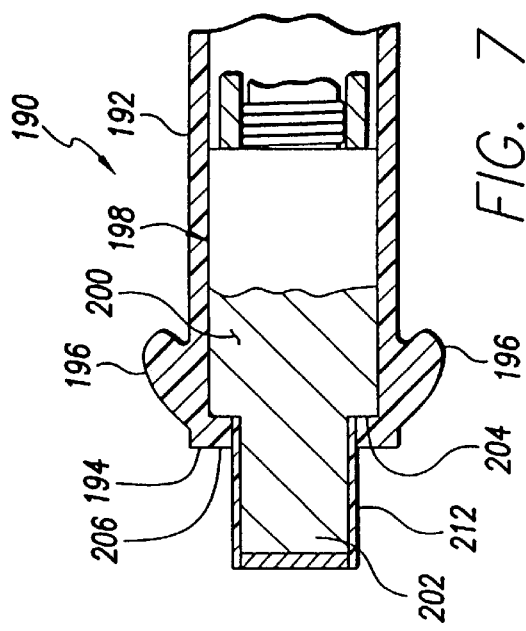
FIG. 7 is a side view, in cross section, of the distal end portion of a lead assembly in accordance with a fifth embodiment of the invention.

The following description presents the preferred embodiments of the invention representing the best modes contemplated for practicing the invention. This description is not to be taken in a limiting sense but is made merely for the purpose of describing the general principles of the invention whose scope is defined by the appended claims. Moreover, the contexts in which the invention is shown and described herein, that is, specific implantable bipolar pacing and sensing leads, are illustrative only; it will be understood by those skilled in the art that the invention may be used in a wide variety of unipolar, multipolar and other body implantable tissue stimulating leads.

Referring now to FIGS. 1 and 2 of the drawings, there is shown a bipolar, endocardial pacing and sensing lead assembly 10 having a longitudinal axis 12, a proximal end portion 16, a distal end portion 14, and an intermediate portion 18 connecting the end portions 14 and 16. The lead assembly 10 is covered by a tubular insulating housing or sheath 20 made of an insulating, biocompatible, biostable elastomeric material such as polyurethane or silicone rubber. The sheath 20 has a distal extremity 22. The proximal end portion 16 of the lead assembly 10 is adapted to be plugged into the socket or receptacle of a pulse generator 24 and for this purpose the elastomeric sheath 20 includes longitudinally space sets of annular ribs 26 for engaging the wall of the receptacle thereby sealing the receptacle against the entry of body fluids.

The proximal end portion 16 of the lead assembly 10 includes an electrical connector pin 28 and an electrically conductive ring 30. As is well known, the pin 28 and the conductive ring 30 are adapted to engage corresponding terminals within the receptacle of the pulse generator 24.

The lead assembly 10 includes coaxial, inner and outer electrical conductor coils 32 and 34, respectively, electrically isolated from each other by a tubular insulating layer 36 interposed between the coils. The outer conductor 34 has a proximal end 38 electrically connected to the conductive ring 30 and a distal end 40 electrically connected to a ring electrode 42. The inner conductor 32 has a proximal end 44 electrically connected to the connector pin 28 and a distal end 46 extending beyond the distal end of the outer conductor 34 for connection to a tip electrode body 50 (FIG. 2). The tip electrode body 50 and the ring electrode 42 pass electrical pacing stimuli developed by the pulse generator 24 to the heart and/or transmit naturally occurring electrical signals from the heart to the pulse generator. The tip electrode body 50 and the ring electrode 42 are preferably formed of a biocompatible conductive material such as stainless steel, MP35N, platinum, platinum-iridium, titanium or an equivalent material.

As well known in the art, each of the coil conductors 32 and 34 may comprise a multifilar conductor for redundancy to provide continued stimulation and sensing in the event one of the conductor strands breaks. Further, the connector pin 28 on the proximal end portion of the lead assembly is hollow so that in accordance with well known implantation techniques, a stylet (not shown) may be passed through the hollow connector pin and the central cavity or lumen of the inner conductor coil 32 to enable the physician to maneuver the distal end portion 14 of the lead assembly 10 to position the tip electrode under fluoroscopy to a desired location in the heart.

As best seen in the detailed view in FIG. 2, the tip electrode body 50 comprises a main portion 52 preferably having a generally cylindrical configuration coaxial of the longitudinal axis 12 of the lead assembly. Projecting forwardly from the main portion 52 of the tip electrode body 50 and disposed coaxial therewith is a generally cylindrical tip electrode 54 having a cylindrical side surface 56 and a planar, disk-shaped end surface 58 which comprises the active electrode surface. The diameter of the tip electrode 54 is less than that of the main portion 52 of the tip electrode body 50 so as to define at their junction a radially extending annular planar face 60 on the distal extremity of the main portion 52 of the tip electrode body 50. The annular face 60 is substantially coplanar or flush with the distal extremity 22 (FIG. 1) of the lead assembly sheath 20.

Covering substantially the entire cylindrical side surface 56 of the tip electrode body 50 is a thin dielectric insulative layer 62 which may comprise, by way of example, a parylene coating or a sleeve made of silicone or other insulative material. This insulating layer 62 masks the bulk of the surface of the tip electrode 54 to insure that only the disk-shaped end surface 58 thereof is active with the result that the pacing impedance and current density of the electrode is increased and the stimulation thresholds kept low. Alternatively, the insulating layer 62 may comprise tantalum oxide applied over the entire surface of the tip electrode 54 by sputtering or electrolysis followed by grinding of the distal extremity to expose the disk-shaped active end surface 58.

To reduce polarization voltages, the disk-shaped end surface 58 of the tip electrode 54 may be roughened or texturized or otherwise made porous and/or microporous and/or can be provided with a conductive coating 64 of such materials as titanium nitride, titanium oxide, iridium oxide, platinum black or carbon. All of these materials are known to increase the true electrical surface area to improve the efficiency of electrical performance by reducing wasteful electrode polarization. The disk-shaped surface 58 of the tip electrode 54 can be fabricated to include dimples, grooves, or micropores or other indentations or recesses in the tip electrode surface for promotion of tissue in-growth to enhance anchoring the lead tip to the tissue. Such indentations can also be used to carry drugs or medications for delivery to the adjoining tissue.

The tip electrode 54 of the embodiment of FIGS. 1 and 2 comprises a proximal portion 70 and a distal portion 72. Mounted on the proximal portion 70 of the tip electrode 54 is a drug dispensing element 74 in the form of a monolithic controlled release device (MCRD). The MCRD 74 carried by the tip electrode 54 retains the drug to be dispensed and allows elution thereof at a controlled rate at the body stimulation site. In the context of a pacing lead, the drug may be one countering such reactions as thrombus formation, fibrosis, inflammation or arrhythmias, or any combination thereof. In the preferred embodiment of FIGS. 1–3, the MCRD 74 is in the form of a steroid collar loaded, for example, with a steroidal anti-inflammatory such as dexamethasone. The steroid collar is preferably adhesively bonded to the insulating layer 62 by means of a medical adhesive. The steroid collar 74 has a proximal, radially extending surface 76 perpendicular to the longitudinal axis 12 of the lead assembly, that abuts the radial planar surface 60 on the main portion 52 of the tip electrode body 50 and the distal extremity 22 of the sheath 20 (FIG. 1). The resulting minimization of fibrosis allows the disk-shaped end surface 58 and excitable tissue to be in closer proximity. The result of this suppressed foreign body reaction is lower voltage and current requirements at threshold.

Extending proximally from the main portion 52 of the tip electrode body 50 is a smaller diameter projection 80 received by the distal end 46 of the inner coil conductor 32. The inner coil windings engage the outer surface of the projection 80 and are held in place by a crimp tube 82 in a fashion well known in the art to assure a secure, reliable electrical connection between the conductor coil 32 and the tip electrode body 50. The tip electrode body 50 further includes a small diameter bore 84 coaxial with the lead assembly axis 12, extending forwardly from the proximal extremity of the tip electrode body 50 along a portion of the length thereof for receiving the distal extremity of a stylet which, as explained, assists in the placement of the tip electrode during implantation.

By way of example and not limitation, the diameter of the tip electrode 54 may be approximately 0.043 inch (1.09 mm) providing a small active surface area or microdisk of about 0.94 mm². The distal portion 72 of the tip electrode 54 may be about 0.058 inch (1.47 mm) prior to soaking and swelling of the steroid collar 74, in accordance with this specific example. These dimensions can, of course, be varied, and can include substantially smaller tip electrode diameters, for example, 0.031 inch (0.79 mm). Certain limitations on the length of the exposed or distal portion 72 of the tip electrode 54 should be noted. If this length is too small at the outset (that is, before soaking and swelling of the steroid collar 74), when the collar swells the collar may project past the disk-shaped end surface 58 of the tip electrode 54 so that contact between the disk-shaped end surface 58 and the tissue may be lost. On the other hand, if the length of the exposed or distal portion 72 of the tip electrode is excessive, the active end surface 58 of the tip electrode may be too far from the drug delivery system. There is further the danger of puncturing heart tissue with a small diameter, excessively exposed distal tip portion and difficulties in inserting the lead assembly through the venous system may be encountered.

Again by way of example only, the pre-soak outer diameter of the steroid collar 74 may be of the order of 0.084 inch (2.13 mm) with a length of 0.059 inch (1.50 mm).

The sheath 20 includes a plurality of pliant, main tines 90 projecting rearwardly from the sheath and disposed at an acute angle thereto. Preferably, the main tines 90 are molded as part of the sheath. The tines 90 serve to anchor the tip electrode body 50 once in place within a chamber of the heart. As is well known, during implantation, as the distal end portion 14 of the lead assembly 10 is advanced within a vein toward the heart, the pliant tines 90 are urged by the wall of the vein to move down into contact with the outer surface of the sheath. The angularly oriented tines 90 engage heart tissue so as to urge the disk-shaped end surface 58 into contact with the endocardium in a direction parallel to the lead axis 12. Although any number of tines may be used, four are preferably used in the embodiment of FIGS. 1 and 2.

In addition to the main tines 90, there is also included in accordance with another aspect of the invention a set of nubby tines 92 adjacent the main tines 90. This additional or auxiliary set of tines 92 increases the surface area of the portion of the lead assembly engaging the trabecular network inside the heart to augment the stabilization and fixation of the tip electrode 54 and thereby avoid microdislodgment which may result in sporadic reduction or loss of electrical contact between the disk-shaped end surface 58 and the endocardium. Four auxiliary tines 92 are provided in the preferred embodiment of FIGS. 1 and 2, but it will be evident that a greater or lesser number may be used.

FIG. 3 shows in cross-section an example of the size and shape of a steroid collar 74 after an extended period of soaking. The length of the steroid collar 74 has swollen to approximately 0.077 inch (1.96 mm) while its diameter has increased to about 0.110 inch (2.79 mm). To minimize the swelling of the collar 74, the collar is preferably fabricated of a non-porous polymer.

With reference now to FIG. 4, there is shown the distal portion 100 of a lead assembly in accordance with an alternative embodiment of the present invention. The distal end portion 100 includes a tip electrode body 102 having a tip electrode 104 as previously described. The tip electrode 104 has a distal portion 106, a proximal portion 108, and MCRD in the form of a steroid collar 110 mounted on, and adhesively secured to, the proximal portion 108 of the tip electrode 104. In this embodiment, the steroid collar 110 itself includes a set of auxiliary nubby tines 102 formed integrally with the collar and projecting from the outer surface thereof. Such auxiliary tines 102 can be used instead of or in addition to the auxiliary tines 92 shown in FIGS. 1–3.

FIG. 5 shows the distal end portion 120 of still another embodiment of a lead assembly in accordance with the present invention. The distal end portion 120 includes a tip electrode body 122 having a main portion 124, a tip electrode 126 of smaller diameter than the main portion 124 projecting distally therefrom and a proximal projection 128 for receiving the distal windings of a conductor coil 130. The main portion 124 of the tip electrode body 122 includes a central, reduced diameter or necked-down region 132 circumscribing the main portion 124. The tip electrode 126, as in the embodiments of FIGS. 1–4, includes a proximal portion 134 and a distal portion 136. An MCRD in the form of a cylindrical steroid collar 138 having a distal extremity or face 140 is carried by the proximal portion 134 of the tip electrode 126. The lead assembly of FIG. 5 further includes an outer insulating sheath 142 having a distal end 144 extending over the steroid collar 138. The sheath 142 includes a distal extremity 146 flush with the distal extremity 140 of the steroid collar 138. It will thus be seen that the distal end 144 of the sheath covers the outer, cylindrical surface of the steroid collar 138. To stabilize the position of the sheath 142 relative to the tip electrode body 122, the sheath 142 includes an inner wall 148 having an annular, ring-like inwardly directed projection 150 nested within the necked-down region 132 of the main portion 124 of the tip electrode body. It will thus be seen that the distal end 144 of the sheath and the tip electrode body 122 are interlocked so as to restrict relative motion between these two elements.

Figure 6:
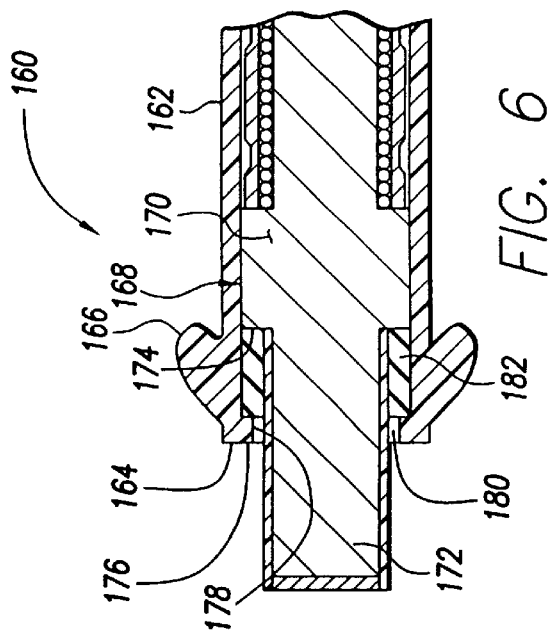
FIG. 6 is a side view, in cross section, of the distal end portion of a lead assembly in accordance with a fourth embodiment of the invention.

FIG. 6 shows the distal end portion 160 of a lead assembly pursuant to still another embodiment of the present invention. The lead assembly of FIG. 6 includes an outer insulative sheath 162 including a distal extremity 164 and a set of nubby, auxiliary tines 166 adjacent thereto. The lead assembly of FIG. 6 further includes a tip electrode body 168 including, as before, a main cylindrical portion 170, a coaxial tip electrode 172 having a smaller diameter than that of the main portion 170, and a planar, annular radially extending surface 174 along the distal extremity of the main portion 170. The sheath 162 has at its distal extremity 164 a distal, inwardly-directed wall 176 provided with an aperture 178 through which the tip electrode 172 extends. The diameter of the aperture 178 is larger than the diameter of the tip electrode 172 so as to define an annular gap or passage 180 through which a drug may be eluted from an MCRD in the form of a steroid collar 182 carried between the annular surface 174 and the sheath wall 176.

FIG. 7 shows the distal end portion 190 of a lead assembly in accordance with yet another embodiment of the invention. The lead assembly of FIG. 7 includes an outer insulating sheath 192 including a distal extremity 194 and a set of auxiliary tines 196 adjacent thereto. The lead assembly of FIG. 7 further includes a tip electrode body 198 including, as before, a main cylindrical portion 200, a coaxial tip electrode 202 having a smaller diameter than that of the main portion 200, and a planar, annular radially extending surface 204 on the main portion 200 at the distal extremity thereof. The sheath 192 includes an inwardly directed wall 206 at the distal extremity 194 of the sheath, similar to that of the embodiment of FIG. 6. The inwardly directed wall 206 permits the tip electrode 202 to project therethrough, and unlike the embodiment of FIG. 6, engages with the insulative layer 212 on the side of the tip electrode 202. The embodiment of FIG. 7 does not have a steroid collar. Instead, the tip electrode body 198 or only the tip electrode 202, in accordance with techniques well known in the art, may be fabricated of a porous material (such as sintered forms of the metals and alloys mentioned above) loaded with a steroidal anti-inflammatory or other drug so as to function as an MCRD.

Figure 8:
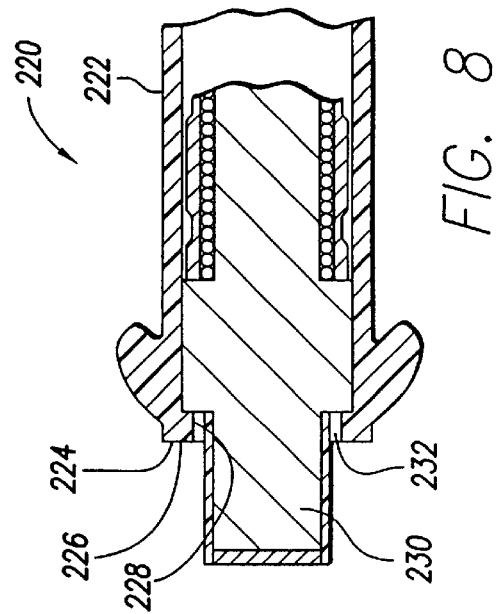
FIG. 8 is a side view, in cross section, of the distal end portion of a lead assembly in accordance with a sixth embodiment of the invention.

FIG. 8 shows the distal end portion 220 of a lead assembly in accordance with yet another embodiment similar in all respects to that of FIG. 7 except that the insulating sheath 222 in FIG. 8 includes at its distal extremity 224 an inwardly directed wall 226 having a central aperture 228 larger than the tip electrode 230 so as to define an annular gap or passage 232 through which a drug carried by the porous tip electrode body may be eluted.

It should be appreciated that the foregoing description is only illustrative of the invention. Various alternatives and modifications can be devised by those skilled in the art without departing from the spirit of the invention. Accordingly, the present invention is intended to embrace all such alternatives, modifications and variations as fall within the scope of the appended claims.

What is claimed is:

1. A passive fixation body implantable lead assembly adapted to transmit electrical signals between a proximal end portion of the lead assembly and a distal end portion of the lead assembly and to thereby stimulate selected body tissue and/or sense electrical signals therefrom, the lead assembly having a longitudinal axis and comprising:

an electrical conductor extending between said proximal and distal end portions of the lead assembly for transmitting the electrical signals, the conductor having a distal end;

a sheath of insulative, biocompatible material enclosing the electrical conductor for electrically insulating the conductor from body tissue and body fluids, the insulative sheath having a distal extremity;

a tip electrode electrically connected to the distal end of the electrical conductor, the tip electrode being in the form of a cylinder disposed coaxially of the longitudinal axis of the lead assembly, the tip electrode having a side surface and a distal extremity comprising a generally planar active electrode surface extending substantially perpendicular to the longitudinal axis of the assembly; and a thin dielectric insulating layer covering substantially the entire side surface of the tip electrode.

2. A lead assembly, as defined in claim 1, in which:

the active electrode surface at the distal extremity of the tip electrode has an area less than about 1 mm$^2$.

3. A lead assembly, as defined in claim 1, in which:

the active electrode surface of the tip electrode is coated with a material that reduces polarization.

4. A lead assembly, as defined in claim 1, in which:

the side surface of the tip electrode includes a distal portion and a proximal portion; and a drug dispensing member is disposed around the proximal portion of the tip electrode for storing a drug to be dispensed to the body tissue.

5. A lead assembly, as defined in claim 4, in which:

the drug dispensing member is in the form of a collar disposed about the tip electrode, and in which a first plurality of tines extends outwardly from said collar; and a second plurality of tines extends outwardly from said sheath and away from the tip electrode to form an acute angle with the sheath material, said second plurality of tines being disposed proximally of said first plurality of tines along the distal end portion of the lead assembly, the first plurality of tines having a length less than that of the second plurality of tines.

6. A lead assembly, as defined in claim 1, in which:

the tip electrode is fabricated of a porous material adapted to retain and dispense a therapeutic drug.

7. A lead assembly, as defined in claim 6, in which:

the distal extremity of the insulative sheath includes an inwardly directed wall, the wall having a central aperture, the porous tip electrode extending through said aperture.

8. A lead assembly, as defined in claim 7, in which:

the aperture of the inwardly directed wall of the insulative sheath is defined by a surface in contact with the outer side surface of the body of the tip electrode, the porous material of the tip electrode body permitting dispensing of the drug.

9. A lead assembly, as defined in claim 7, in which:

the aperture of the inwardly directed wall of the insulative sheath is defined by a surface, the aperture-defining surface being spaced from the outer side surface of the tip electrode to allow dispensing of the drug through the space defined by the aperture defining surface and the side surface of the tip electrode body.

10. A lead assembly, as defined in claim 1, in which the sheath includes:

a first plurality of tines extending outwardly from said sheath, said first plurality of tines being disposed adjacent the distal extremity of the sheath; and a second plurality of tines extending outwardly from said sheath and away from the tip electrode to form an acute angle with the sheath material, said second plurality of tines being disposed proximally of said first plurality of tines along the distal end portion of the lead assembly, the first plurality of tines having a length less than that of the second plurality of tines.

11. A passive fixation body implantable lead assembly adapted to transmit electrical signals between a proximal end portion of the lead assembly and a distal end portion of the lead assembly and to thereby stimulate selected body tissue and/or sense electrical signals therefrom, the lead assembly having a longitudinal axis and comprising:

an electrical conductor extending between said proximal and distal end portions of the lead assembly for transmitting the electrical signals, the conductor having a distal end;

a sheath of insulative, biocompatible material enclosing the electrical conductor for electrically insulating the conductor from body tissue and body fluids, the insulative sheath having a distal extremity;

a tip electrode electrically connected to the distal end of the electrical conductor, the tip electrode being coaxial of the longitudinal axis of the lead assembly and having a proximal portion, a distal portion and a distal extremity comprising a generally planar active electrode surface extending substantially perpendicular to the longitudinal axis of the assembly; and a drug dispensing annular member disposed around the proximal portion of the tip electrode for storing a drug to be dispensed to the body tissue.

12. A lead assembly, as defined in claim 11, in which:

the tip electrode is substantially cylindrical, the planar active electrode surface at the distal extremity of the tip electrode body comprising a disc-shaped area and the drug dispensing member comprising an annular collar.

13. A lead assembly, as defined in claim 12, in which:

the drug dispensing member comprises a material whose swelling is minimal when placed in contact with body fluids.

14. A lead assembly, as defined in claim 12, in which:

the drug dispensing member is bonded to the proximal portion of the tip electrode body.

15. A lead assembly, as defined in claim 11, in which:

the active electrode surface at the distal extremity of the tip electrode has an area less than about 1 $mm^2$.

16. A lead assembly, as defined in claim 11, in which:

the active electrode surface of the tip electrode is coated to reduce polarization.

17. A lead assembly, as defined in claim 11, in which:

the tip electrode has an outer, side surface, the side surface being coated with a thin dielectric insulating material.

18. A lead assembly, as defined in claim 11, in which:

the distal portion and at least part of the proximal portion of the tip electrode project from the distal extremity of the insulative sheath.

19. A lead assembly, as defined in claim 18, in which:

the drug dispensing member is disposed distally of the distal extremity of the insulative sheath.

20. A lead assembly, as defined in claim 18, in which:

at least a portion of the drug dispensing member is disposed within the insulative sheath.

21. A lead assembly, as defined in claim 20, in which:

the drug dispensing member is disposed in its entirety within the insulative sheath immediately adjacent the distal extremity thereof.

22. A lead assembly, as defined in claim 21, in which:

the distal extremity of the insulative sheath includes an inwardly directed wall, the wall having a central aperture, the tip electrode extending through said aperture.

23. A lead assembly, as defined in claim 22, in which:

the tip electrode has an outer side surface, the aperture of the inwardly directed wall of the insulative sheath being defined by a surface, the aperture-defining surface being spaced from the outer side surface of the tip electrode body to allow dispensing of the drug through the space defined by the aperture defining surface and the side surface of the tip electrode body.

* * * * *